United States Patent [19]

Shaw et al.

[11] Patent Number: 4,824,961

[45] Date of Patent: Apr. 25, 1989

[54] PRODUCTION OF SUBSTITUTED 1,3,4,9-TETRAHYDROPYRANO(3,4-B)INDOLE-1-ACETIC ACIDS

[75] Inventors: Chia-Cheng Shaw; Karel Pelz, both of Quebec, Canada

[73] Assignee: American Home Products Corporation, New York, N.Y.

[21] Appl. No.: 89,881

[22] Filed: Aug. 27, 1987

[51] Int. Cl.$^4$ .......................................... C07D 493/04
[52] U.S. Cl. ................................. 548/432; 548/502; 548/509
[58] Field of Search .............. 548/494, 509, 432, 502

[56] References Cited

U.S. PATENT DOCUMENTS

| | | | |
|---|---|---|---|
| 3,843,681 | 10/1974 | Demerson et al. | 548/432 |
| 3,939,178 | 2/1976 | Demerson et al. | 548/432 |
| 3,974,179 | 8/1976 | Demerson et al. | 514/870 |
| 4,670,462 | 6/1987 | Katz et al. | 514/411 |

*Primary Examiner*—Mary E. Ceperley
*Attorney, Agent, or Firm*—Walter Patton

[57] ABSTRACT

Process for the production of substituted 1,3,4,9-tetrahydropyrano[3,4-b]indole-1-acetic acids having useful analgesic and anti-inflammatory activity.

7 Claims, No Drawings

PRODUCTION OF SUBSTITUTED 1,3,4,9-TETRAHYDROPYRANO(3,4-B)INDOLE-1-ACETIC ACIDS

BACKGROUND OF THE INVENTION a. Field of Invention

This invention relates to novel processes for the production of indole derivatives.

More specifically, this invention relates to the process for the production of tricyclic acetic acid derivatives in which the tricyclic portion thereof is characterized by having an indole portion fused to a pyrano ring. Still more specifically, the process of this invention produces the following tricyclic acetic acid system:

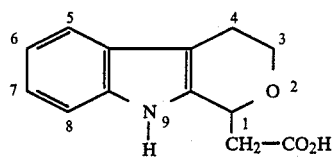

designated 1,3,4,9-tetrahdropyrano[3,4-b]indole-1-acetic acid in which the carbons at the 1- and 4-position, and optionally at the 5-, 6-, and 8-positions are further substituted.

The indole derivatives produced by the present process are described in Katz et al, U.S. Pat. No. 4,670,462 and U.S. Pat. No. 4,775,690, and are herein incorporated by reference.

The indole derivatives produced by the present process are known to exhibit useful pharmacodynamic properties without eliciting undesirable side effects. Notable attributes of these derivatives are anti-inflammatory and analgesic activities.

b. Prior Art

The closest prior art to the present invention is:

Katz et al, U.S. Pat. No. 4,670,462 and U.S. Pat. No. 4,775,690; and Demerson et al, U.S. Pat. No. 3,939,178.

Demerson et al disclosed the production of 1,3,4,9-tetrahydropyrano[3,4-b]indoles and 1,3,4,9-tetrahydrothiopyrano[3,4-b]indoles having analgesic and anti-inflammatory activity. Related U.S. Pat. Nos. are 3,974,179 and 3,843,681.

SUMMARY OF THE INVENTION

The process of the present invention is directed to the production of the compounds represented by formula (I)

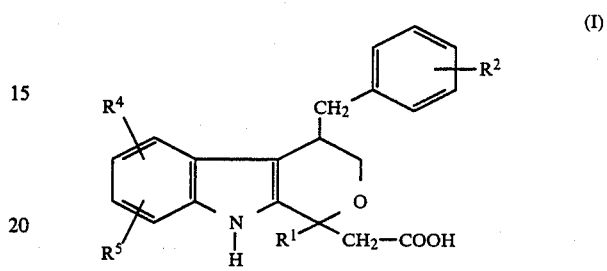

wherein $R^1$ is lower alkyl containing 1 to 4 carbon atoms; $R^4$ and $R^5$ are hydrogen, lower alkyl containing 1 to 6 carbon atoms, or halogen; and $R^2$ is 4-halogen, 2- and 4-dihalogen, 3-trifluoromethyl, or 4-methoxy; and the pharmaceutically acceptable salts thereof.

The preferred process of the present invention is directed to the production of the compound designated 1-ethyl-1,3,4,9-tetrahydro-4-(phenylmethyl)-pyrano[3,4-b]indole-1-acetic acid, and the pharmaceutically acceptable salts thereof.

A still further preferred aspect of the present invention is directed to the prodution of cis-1-ethyl-1,3,4,9-tetrahydro-4-(phenylmethyl)-pyrano[3,4-b]indole-1-acetic acid, and the pharmaceutically acceptable salts thereof.

The processes of the present invention are represented by the following flow sheets:

Process A

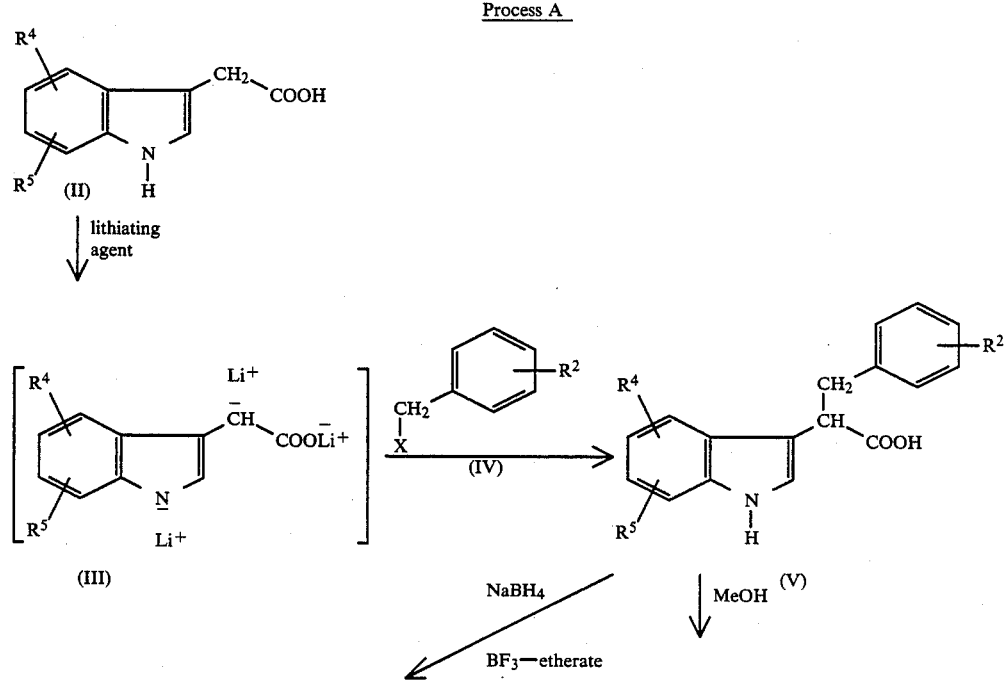

Process A
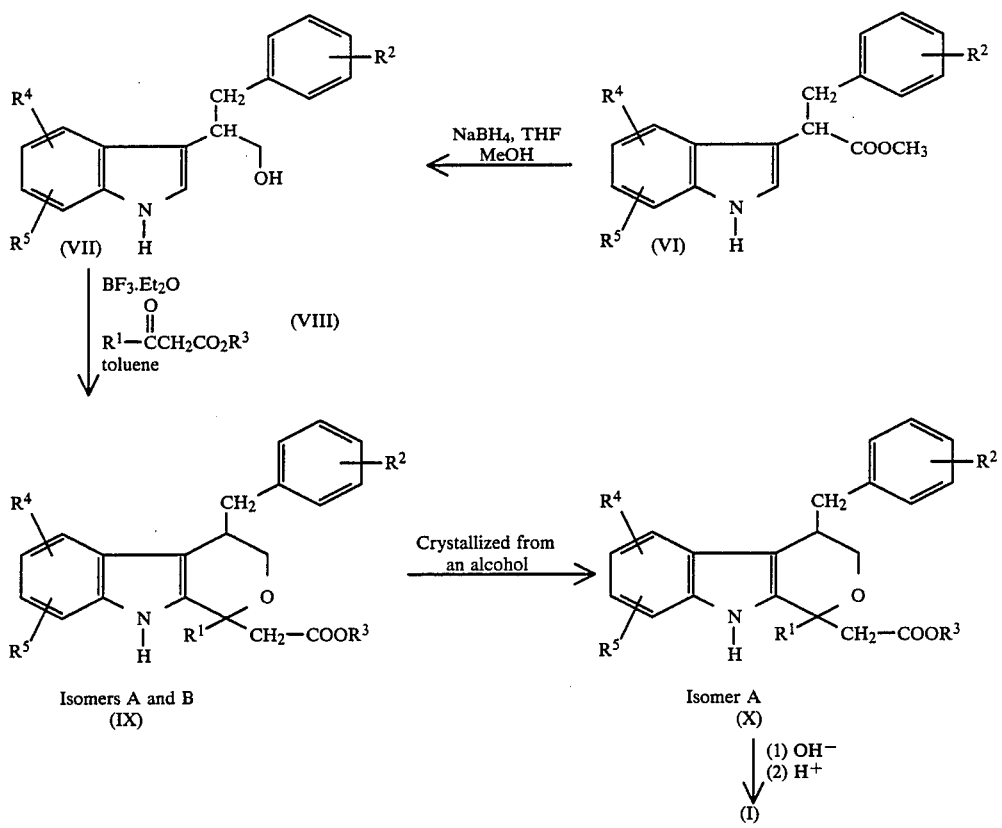
wherein $R^1$, $R^2$, $R^4$, and $R^5$ are as defined above; $R^3$ is lower alkyl containing 1 to 8 carbon atoms; and X is chlorine, bromine or iodine.
Process B
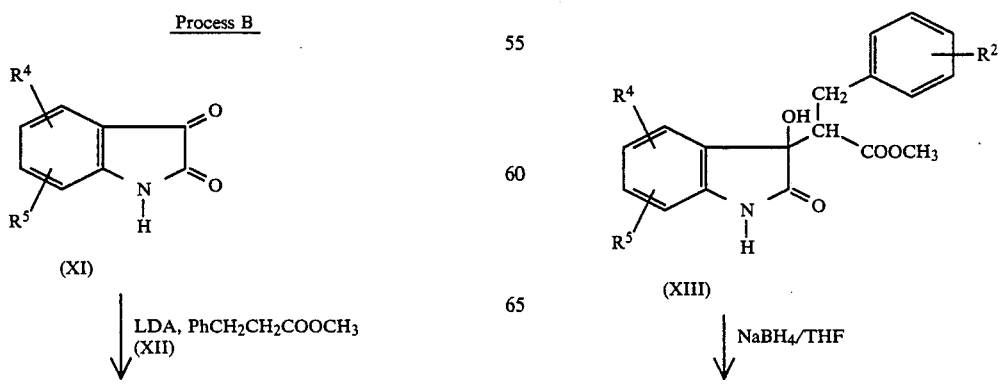

-continued
Process B

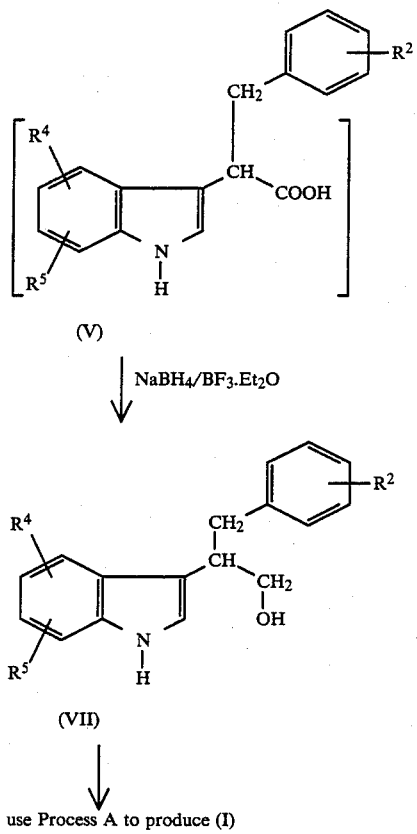

wherein $R^2$, $R^4$, and $R^5$ are as defined above.

Referring to process A, substituted indole-3-acetic acid (II) was directly lithiated with about 4 molar equivalents of lithium diisopropylamide in THF at −5° to −10° C. to generate the substituted synthon lithium 1, α-dilithioindole-3-acetate (III). The alkylation of (III) with a large excess of substituted benzyl halide (IV) afforded the substituted α-benzylindole-3-acetic acid (V) in high crude yield. The crude acid (V) was converted to the corresponding methyl ester (VI) in high yield and purity.

The present process has the following advantages:
1. the lithiation reaction can be carried out at temperatures of −5° to −10° C., which is conveniently attained in a pilot plant;
2. there is no lump formation in the lithiation reaction; and
3. the products [acid (V) or methyl ester (VI)] can be isolated in high yield and high purity with no dimer formation.

The substituted lithium 1, α-dilithioindole-3-acetate (III) can also be generated in situ in THF by using 4 molar equivalents of n-butyllithium at −78° C., then warming to −40° C., for form a yellow solution, according to W. Adam, et al, J. Org. Chem., 45 447 (1980).

Reduction of the substituted methyl α-benzylindole-3-acetate (VI) to the corresponding substituted β-benzyltryptophol (VII) was accomplished in a high yield with lithium aluminum hydride or with sodium borohydride. Sodium borohydride is preferred because it is less hazardous.

In a preferred alternate process, substituted α-benzylindole-3-acetic acid (V), prepared according to Process A, was directly reduced to substituted β-benzyltryptophol (VII) by means of NaBH₄ and BF₃-etherate (in situ formation of diborane), thus making the process one step shorter.

The reduction was complete in about 2 hours at 20 C. as compared with about 25 hours at reflux for the NaBH₄-reduction of the substituted methyl α-benzylindole-3-acetate (VI).

Production of the ester (IX) was preferably carried out by reaction of the substituted β-benzyltryptophol (VII) with 3-oxo-2-alkanoic acid, alkyl ester of formula (VIII) at about −15° C. in toluene.

Production of the ester (IX) was preferably done by a reversed addition of the substituted β-benzyltryptophol (VII) in toluene solution to a cold mixture of the 3-oxo-2-alkanoic acid, alkyl ester (VIII) and boron trifluoride etherate in toluene. The advantage of the reversed addition is that the product (IX) isolated had a more constant ratio of the two isomers A and B. The ratio of the two diastereomers A and B is about 2.1:1 in favor of the desirable isomer A.

The starting material (VII) and the product (IX) are not stable in solution, in the presence of boron trifluoride etherate, thus, prolonged reaction times at higher temperatures should be avoided to prevent formation of polar impurities. The crude product (IX), without filtration through silica gel, was directly fractionally crystallized to obtain the pure crystalline product (X) isomer A.

The product (X) isomer A was subjected to basic hydrolysis and upon acidification the product (I) was obtained in high yield. The final purification of (I) was carried out by recrystallization from aqueous alcohols preferably from ethanol/water or isopropanol/water.

Referring to Process B, in the reaction of isatin (XI) with methyl 3-phenylpropionate (XII), good yields were obtained by reversed quenching at slightly acidic pH, i.e., addition of the reaction mixture to an aqueous solution containing acetic acid in order to minimize reverse aldolization in alkaline aqueous medium.

For the reduction of compound (XIII) to tryptophol (VII), the safe and inexpensive sodium borohydride and borontrifluoride etherate regents were used. This reduction proceeds in two stages. First, compound (XIII) is readily and quantitatively reduced and simultaneously the ester is hydrolyzed by NaBH₄ in dry THF to give the benzylindolylacetic acid (V). Subsequent addition of BF₃.Et₂O completes in about two hours the reduction of the carboxylic group to the primary alcohol, and β-benzyltryptophol (VII) is obtain in a good yield of 57.0% overall from isatin.

For comparison, reduction with lithium aluminum hydride produced tryptophol (VII) in variable yields ranging from 25% to 49% overall from isatin.

It should be noted that direct reduction of ester (XIII) with diborane requires about 15 hours at reflux for completion and the yields are inferior to the above two-stage method.

Sodium bis(2-methoxyethoxy)aluminum hydride may be used for the reduction of ester (XIII), but the yield is lower and the reagent is expensive.

The β-benzyltryptophol (VII) produced by Process B is converted to the final product (I) by the Process A.

The compounds of formula (I) form salts with suitable pharmaceutically acceptable inorganic and organic bases. The acid of formula (I) is transformed in excellent yield into the corresponding pharmaceutically acceptable salts by neutralization of said acid with the appropriate inorganic or organic base. Suitable inorganic bases to form these salts include, for example, the hydroxides, carbonates, bicarbonates, or alkoxides of the alkali metals, or alkaline earth metals, for example, sodium, potassium, magnesium, calcium, and the like. Suitable organic bases include the following amines; lower mono-, di- and tri-alkylamines, the alkyl radicals of which contain up to three carbon atoms, such as methylamine, dimethylamine, trimethylamine, ethylamine, di- and triethylamine, methylethylamine, and the like; mono, di- and trialkanolamines, the alkanol radicals of which contain up to three carbon atoms, such as mono-, di- and triethanolamine; alkylenediamines which contain up to six carbon atoms, such as hexamethylenediamine; amino sugars, such as flucosamine; cyclic saturated or unsaturated bases containing up to six carbon atoms, such as pyrrolidine, piperidine, morpholine, piperazine, and their N-alkyl and N-hydroxyalkyl derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyltrimethanol, and trimethyl-monoethanol) and cyclic ammonium salts, for example the N-methylpyridinium, N-methyl-N-(2-hydroxyethyl)-morpholinium, N,N-dimethylmorpholinium, N-methyl-N-(2-hydroxyethyl)-morpholinium, N,N-dimethylpiperidinium salts, which are characterized by good water-solubility.

The transformations to the salts can be carried out by a variety of methods known in the art. For example, in the case of salts of inorganic bases, it is preferred to dissolve the acid of formula (I) in water containing at least one equivalent amount of a hydroxide, carbonate, or bicarbonate. Preferably, the reaction is performed in a water-miscible organic solvent inert to the reaction conditions, for example, methanol, ethanol, dioxane, and the like in the presence of water. For example, such use of sodium hydroxide, sodium carbonate, or sodium bicarbonate gives a solution of the sodium salts. Evaporation of the solution or addition of a water-miscible solvent of a more moderate polarity, for example, a lower alkanol, for instance, butanol, or a lower alkanone, for example, ethyl methyl ketone, gives the solid salt if that form is desired.

To produce an amine salt, the acid of formula (I) is dissolved in a suitable solvent of either moderate or low polarity, for example, ethanol, acetone, ethyl acetate, diethyl ether, or benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

Included in the present invention is the process for the production of diastereoisomers of compound (I) wherein the 4-substituent is either cis or trans to the acetic acid chain at position one. When the structure of the diastereomers is not known, they are designated Isomer A and B.

Also included in this invention is the process for the resolution of the compounds of formula (I) into their optical isomers. The optical isomers of the compounds of formula (I) result from asymmetric centers, contained therein. Such isomers can be obtained in substantially pure form by classical separation techniques and by sterically controlled synthesis. Included is the specific case of the resolution of 1-ethyl-1,3,4,9-tetrahydro-4-(phenylmethyl)-pyrano[3,4-b]indole-1-acetic acid into its optical isomers by separation of the corresponding [(IS)-endo]-1,7,7-trimethyl-bicyclo[2.2.1]heptan-2-yl ester followed by basic hydrolysis.

The following examples further illustrate the present invention.

EXAMPLE 1

Process A

Preparation of α-Benzylindole-3-acetic Acid (V: $R^2$, $R^4$ $R^5$=—H)

A flask was flushed with nitrogen and charged with 400 mL of lithium diisopropylamide (LDA) in THF/cyclohexane solution (1.93M, 772 mmol). The solution was cooled to $-5°$ to $-10°$ C. To this cold solution was added a solution of indole-3-acetic acid (33.78 g) in tetrahydrofuran (150 mL) over a period of 1 hour, while maintaining the pot temperature at the range of $-5°$ to $-10°$ C.

After stirring at $-5°$ C. for 2 hours, the reaction mixture was cooled to $-10°$ C., and benzyl chloride (53.6 g) was added over a period of 30 minutes, while maintaining the pot temperature at $-10°$ to $-5°$ C. The reaction temperature was allowed to warm to room temperature, and stirring at this temperature was continued for 18 hours.

The reaction mixture was cooled to $-10°$ C., and 150 mL of water was added. The mixture was evaporated under reduced pressure to remove about 70 mL of THF. To the residual solution was added 200 mL of toluene and 150 mL of water. The aqueous phase was separated; the toluene phase was extracted with 50 mL of water. The combined aqueous phases were cooled to 0° to 10° C. and acidified with 20% hydrochloric acid to pH of about 1 to 2. The mixture was extracted with toluene (100 mL×3); the toluene extracts were combined and washed with water until the aqueous phase was neutral. On evaporation, it afforded 49 grams of product as an off-white solid (95.9% crude yield) m.p. 144°–148° C. (dec.). This material was used for the subsequent reaction without further purification.

An analytical sample was prepared by recrystallization from ether/hexane (1:1) to give pure product as fine white cyrstals, m.p. 152°–154° C.

$^1$H NMR (400 MHz; DMSO-$d_6$): δ 3.06 (dd, 1H), 3.35 (dd, 1H), 4.06 (dd, 1H), 6.96 (ddd, 1H), 7.08 (ddd, 1H), 7.14 (m, 1H), 7.18–7.20 (m, 5H), 7.33 (ddd, 1H), 7.63 (ddd, 1H), 10.93 (b.s., 1H, D$_2$O exchangeable)

IR (KBr): 3390, 1700 cm$^{-1}$

EXAMPLE 2

Process A

Preparation of Methyl α-Benzylindole-3-acetate (VI: $R^2$, $R^4$, $R^5$=—H)

To a solution of α-benzylindole-3-acetic acid (12 g) in methanol (200 mL), was added 2 mL of concentrated H₂SO₄; the mixture was stirred at reflux temperature for 2 hours. The reaction mixture was concentrated under reduced pressure to a volume of about 50 mL, then diluted with 200 mL of toluene. The toluene solution was washed with water, saturated NaHCO₃ solution, and again with water. On evaporation, if afforded 12.3 g (97.6% crude yield) of product as a light brown viscous oil. The crude product slowly crystallized on standing at room temperature. It was triturated with heptane to give fine white crystals, m.p. 62°–68° C.

EXAMPLE 3

Process A

Preparation of β-Benzyltryptophol (VII: $R^2$, $R^4$, $R^5$=—H)

To a solution of methyl α-benzylindole-3-acetate (11.6 g, 92.5% purity) in tetrahydrofuran (60 mL) was added 3.65 g of sodium borohydride in one lot. The mixture was heated with stirring under nitrogen at 65° to 70° C.

To the above refluxing mixture was added dropwise 18 mL of methanol over a period of 8 hours. After the addition, the mixture was stirred at 60° to 70° C. overnight. TLC of a work-up sample showed no starting material. The reaction mixture was cooled to 10° to 15° C. and 60 mL of cold water was added over a 15 minute period. The mixture was stirred for 10 minutes, 100 mL of toluene was added, and the mixture was stirred vigorously for 15 minutes. The aqueous phase was separated and extracted with 50 mL of toluene. The toluene extracts were combined and washed with water (80 mL×2), 10% hydrochloric acid (50 mL) then water (80 mL×4). The organic phase was filtered; the filtrate was evaporated under reduced pressure to afford 9.62 g of product as a beige-colored gum. Gas chromatography analysis of the product showed a purity of 98.8% (98.0% yield).

EXAMPLE 4

Process A

Preparation of β-Benzyltryptophol (VII: $R^2$, $R^4$, $R^5$=—H)

To a solution of 2-(3-indolyl)-3-phenylpropionic acid (2.0 g, 7.55 mmol) in 30 mL tetrahydrofuran was added, by portions, while maintaining the temperature at 20° C. for ½ hour. To this was added, over ½ hour at 20° C., borontrifluoride etherate (4.18 g, 29.44 mmol) and stirred at 20° C. for 2 hours.

To the reaction mixture was added 40 mL toluene, followed by the slow addition of 30 mL water at 20° C. Then 1.5 mL 2NHCl was added to pH=3. The organic phase was separated and washed with 2×25 mL water, then it was evaporated on the rotovap to dryness to yield the product in 93.8% yield.

EXAMPLE 5

Process A

Preparation of cis-1-Ethyl-1,3,4,9-tetrahydro-4-(phenylmethyl)-pyrano[3,4-b]indole-1-acetic Acid Methyl Ester (X: $R^2$, $R^4$, $R^5$=—H; $R^3$=—CH₃)

To a solution of boron trifluoride etherate (10.9 g) in dry toluene (45 mL), cooled to 0° C. was added 5.0 g of methyl propionyl acetate. The mixture was stirred and cooled to −15°±2° C. under nitrogen.

To the above cold soluton was added dropwise, over a period of 30 minutes, a solution of β-benzyltryptophol (9.62 g) in dry toluene (30 mL) while maintaining the pot temperature at −15° to −10° C. After the addition, the mixture was stirred at −15°±2° C. for 4 hours, then left in the cold room (−15° C.) without stirring overnight.

To the cold reaction mixture was added 9 mL of pyridine over a period of 15 minutes while maintaining the pot temperature below +10° C. (a mass of organic salt formed). After the addition, the mixture was stirred for 10 minutes, then 30 mL of cold water was added, and the mixture stirred vigorously for 10 minutes. The aqueous phase was separated and extracted with 40 mL of toluene. The toluene extracts were combined, washed with water (50 mL×2), then 10% hydrochloric acid (40 mL), followed by water (50 mL×3).

The organic phase was filtered and evaporated under reduced pressure to give 13.46 g of crude product as a beige-colored gum.

A quantitative HPLC analysis of this product showed it contained 53.0% of the cis-diastereomer and 25.0% of the trans-diastereomer (ratio of two diastereomers was 2:1). The crude product slowly crystallized on standing at room temperature.

The combined yield of both isomers was 76.4%.

The cis-diastereomer was obtained by crystallization from isopropanol giving 82.3% recovery, m.p. 119.5°–120.5° C. HPLC showed 96.6% cis-isomer and 1.7% trans-isomer.

EXAMPLE 6

Process A

Preparation of cis-1-Ethyl-1,3,4,9-tetrahydro-4-(phenylmethyl)-pyrano[3,4-b]indole-1-acetic Acid (I: $R^2$, $R^4$, $R^5$=—H)

cis-1-Ethyl-1,3,4,9-tetrahydro-4-(phenylmethyl)-pyrano[3,4-b]indole-1-acetic acid methyl ester in 3 parts methanol and aqueous NaOH was refluxed for 45 minutes. The methanol was stripped off and replaced with water/EtOH for a final concentration of 6 parts water and 3 parts EtOH. Acetic acid was added (20% excess based on NaOH) at 50° C. and the crude product was allowed to crystallize at 50° C. Then the pH was adjusted to 2 at 25° C. with hydrochloric acid/water (1:1).

The crude product was filtered and dried at 60° C. for 20 hours to give 95.0% yield, m.p. 145.5–147° (dec). HPLC showed 98.6% purity.

The crude product was recrystallized from isopropanol/water (2:1) to give 99.7% pure product, m.p. 147°–148° C.

EXAMPLE 7

Process B

Preparation of Methyl 2,3-Dihydro-3-hydroxy-α-(phenylmethyl)-2-oxo-1H-indole-3-acetate To a cooled (−5° C.) suspension of isatin (8.85 g, 0.0602 mol), and methyl 3-phenylpropionate (9.88 g, 0.0602 mol) in 220 mL of dry tetrahydrofuran under a nitrogen atmosphere was added lithium diisopropylamide (LDA) (75 mL, 0.1275 mol of a 1.72M solution) over a 1½ hour period. The reaction mixture was stirred at −5° C. for one hour and then poured into a cooled (0° to 5° C.) solution of toluene (140 mL), and acetic acid (30.6 g, 0.51 mol, 300% excess) over a ½ hour period under a nitrogen atmosphere. The transfer was completed with a 200 mL water wash.

The mixture was stirred for ½ hour at 5° to 10° C. at pH 5.5. The aqueous layer was separated and extracted with toluene (140 mL). The combined toluene phases were washed with 10% brine (50 mL) and stirred for ½ hour with activated charcoal (4.4 g). The charcoal was removed by filtration and washed with toluene (2×50 mL). The filtrate was evaporated to dryness in vacuo to give 11.82 g of residue containing 7.48 g of product (yield 68.0%).

EXAMPLE 8

Process B

Preparation of β-Benzyltryptophol (VII: $R^2$, $R^4$, $R^5$=—H)

To a solution of methyl 2,3-dihydro-3-hydroxy-α-(phenylmethyl-2-oxo-1H-indole-3-acetate (3.11 g, 10 mmol) in tetrahydrofuran (40 mL) under a nitrogen atmosphere was added in portions at 25° C., sodium borohydride (0.76 g, 20 mmol). The mixture was stirred at 25° C. for one hour. To this mixture was added, over half an hour at 25° C., borontrifluoride-etherate (3.8 g, 26.6 mmol). The mixture was stirred at 25° C. for 1.5 hours, then it was refluxed for 2 hours, then cooled to 20° C.

To the reaction mixture was added 50 mL toluene, followed by the slow addition of 50 mL 2N HCl, then it was stirred at 25° C. for half an hour. The organic phase was separated and washed with 2×25 mL water, then it was evaporated on the rotovap to dryness to give a residue of 2.82 g containing 2.13 g of β-benzyltryptophol, yield 84.8%.

EXAMPLE 9

Process B

Preparation of β-Benzyltryptophol (VII: $R^2$, $R^4$, $R^5$=—H)

To a solution of crude methyl 2,3-dihydro-3-hydroxy-α-(phenylmethyl)-2-oxo-1H-indole-3-acetate (9.05 g obtained from 4.43 g isatin by the process of Example 7) in tetrahydrofuran (63 mL) under a nitrogen atmosphere was added in portions at 25° C., sodium borohydride (1.79 g). The mixture was stirred at 25° C. overnight. To this mixture was added, over half an hour at 20° C., borontrifluoride-etherate (8.91 g). The mixture was stirred at 20° C. for 2 hours, and then 2 hours at 50° C., then cooled to 20° C.

To the reaction mixture was added 80 mL toluene, followed by the slow addition of 32 mL H2O and 3 mL 2N HCl to pH2. The organic phase was separated and washed with 2×25 mL water, then it was evaporated on the rotovap to dryness to give a residue containing 4.3 g of β-benzyltryptophol, yield 57.0% overall from isatin.

EXAMPLE 10

Process B

Preparation of β-Benzyltryptophol

To a solution of sodium bis(2-methoxyethoxy)aluminum hydride (30.4 mL, 103.48 mmol of a 3.4M solution) in 124 mL dry toluene at 20° C. under a nitrogen atmosphere was added a solution of methyl 2,3-dihydro-3-hydroxy-α-(phenylmethyl)-2-oxo-1H-indole-3-acetate (10 g, 20.31 mmol) dissolved in 12 mL toluene and 28 mL tetrahydrofuran.

The mixture was stirred at 25° C. for 2 hours, then heated slowly to reflux and most of the tetrahydrofuran was distilled off at atmosphereic pressure. The internal temperature was raised to 110° C. The mixture was refluxed for 2 hours, then cooled to 20° C.

To the mixture was added slowly at 20° C., a solution of 44.35 mL sulfuric acid in 205 mL water and stirred for half an hour. The aqueous phase was separated and extracted with 30 mL toluene. The combined organic layers were washed with 3×30 mL water, then stirred with 1 g Norite A for half an hour. The mixture was filtered over Celite and the Celite cake was washed with 2×30 mL toluene. The filtrate was evaporated on the rotovap to dryness to produce 62 -benzyltryptophol in 65.8% yield.

We claim:

1. A process for producing compounds of formula (I)

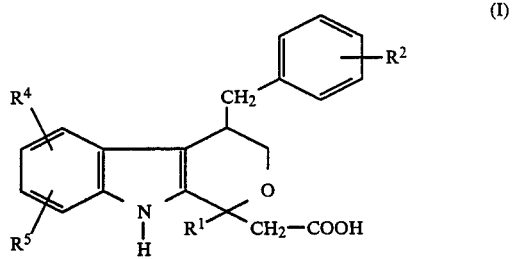

wherein $R^1$ is lower alkyl containing 1 to 4 carbon atoms; $R^4$ and $R^5$ are hydrogen, lower alkyl containing 1 to 6 carbon atoms, or halogen; and $R^2$ is hydrogen, 4-halogen, 2- and 4-dihalogen, 3-trifluoromethyl, or 4-methoxy which comprises the steps (a) lithiating substituted indole-3-acetic acids of formula (II)

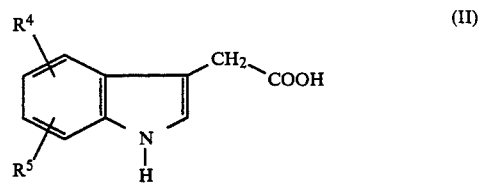

wherein $R^4$ and $R^5$ are as defined above to produce the synthon substituted lithium 1, α-dilithioindole-3-acetate of formula (III)

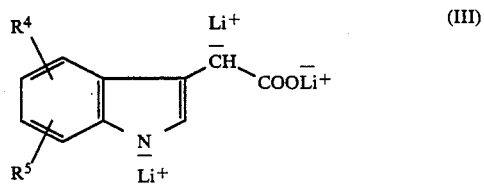

wherein $R^4$ and $R^5$ are as defined above (b) alkylating said synthon (III) with the halide of formula (IV)

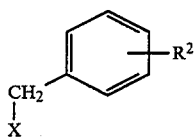

wherein $R^2$ is as defined above and X is halogen selected from the group consisting of chlorine, bromine, and iodine to produce substituted indole-3-acetic acids of formula (V)

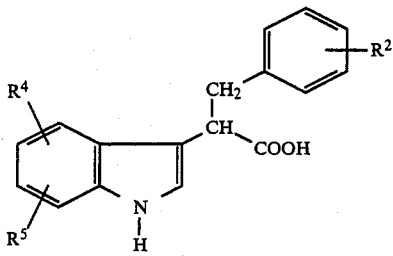

wherein $R^2$, $R^4$, and $R^5$ are as defined above (c) esterifying said substituted indole-3-acetic acids of formula (V) to produce the corresponding ester of formula (VI)

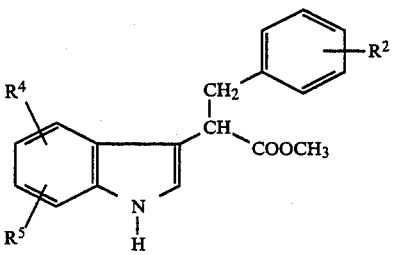

wherein $R^2$, $R^4$, and $R^5$ are as defined above (d) reducing said ester of formula (VI) to produce the substituted β-benzyltryptophol of formula (VII)

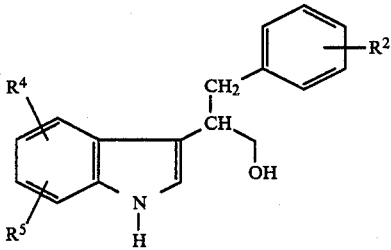

wherein $R^2$, $R^4$, and $R^5$ are as defined above (e) reacting said tryptophol of formula (VII) with 3-oxo-2-alkanoic acid, alkyl ester of formula (VIII)

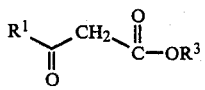

wherein $R^1$ is as defined above and $R^3$ is lower alkyl containing 1 to 8 carbon atoms to produce isomers A and B of the alkyl ester of formula (IX)

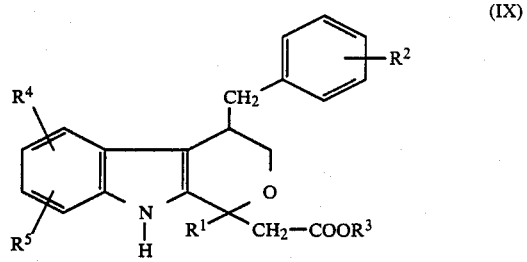

wherein $R^1$, $R^2$, $R^3$, $R^4$, and $R^5$ are as defined above (f) separating said isomer A from isomer B by crystallizing isomer A from an alcohol solvent and hydrolyzing isomer A to obtain the desired compound of formula (I).

2. The process according to claim 1 wherein $R^1$ is ethyl, $R^2$, $R^4$, and $R^5$ are hydrogen.

3. The process according to claim 1 wherein in step (d) the reduction of the ester of formula (VI) is carried out with NaBH₄ in THF with addition of a lower aliphatic alcohol.

4. The process according to claim 1 wherein in step (e) said 3-oxo-2-alkanoic acid, alkyl ester is methyl propionyl acetate and the reaction is carried out in the presence of boron trifluoride etherate.

5. The process according to claim 1 wherein in step (e) a toluene solution of said tryptophol of formula (VII) is added to a cold mixture of 3-oxo-2-alkanoic acid alkyl ester and boron trifluoride etherate in toluene.

6. The process according to claim 1 wherein in step (f) separation of said isomer A from isomer B is carried out by crystallizing isomer A from isopropyl alcohol.

7. A process for producing compounds of formula (I)

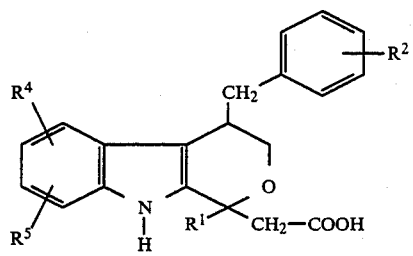

wherein $R^1$ is lower alkyl containing 1 to 4 carbon atoms; $R^4$ and $R^5$ are hydrogen, lower alkyl containing 1 to 6 carbon atoms, or halogen; and $R^2$ is hydrogen, 4-halogen, 2- and 4-dihalogen, 3-trifluoromethyl, or 4-methoxy which comprises the steps (a) lithiating substituted indole-3-acetic acids of formula (II)

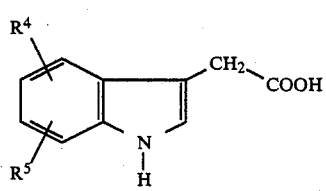

wherein R[4] and R[5] are as defined above to produce the synthon substituted lithium 1, α-dilithioindole-3-acetate of formula (III)

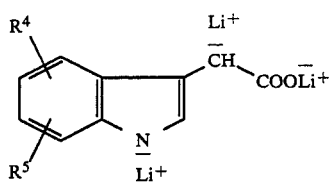
(III)

wherein R[4] and R[5] are as defined above
(b) alkylating said synthon (III) with the halide of formula (IV)

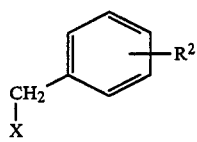
(IV)

wherein R[2] is as defined above and X is halogen selected from the group consisting of chlorine, bromine, and iodine to produce substituted indole-3-acetic acids of formula (V)

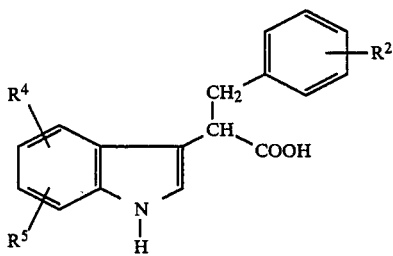
(V)

wherein R[2], R[4], and R[5] are as defined above
(c) reducing the compound of formula (V) with NaBH$_4$ and BF$_3$-etherate to produce a compound of the formula (VII)

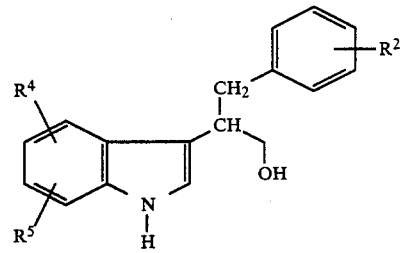
(VII)

wherein R[2], R[4] and R[5] are as defined above
(d) reacting said tryptophol of formula (VII) with 3-oxo-2-alkanoic acid, alkyl ester of formula (VIII)

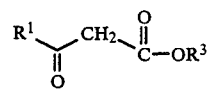
(VIII)

wherein R[1] is as defined above and R[3] is lower alkyl containing 1 to 8 carbon atoms to produce isomers A and B of the alkyl ester of formula (IX)

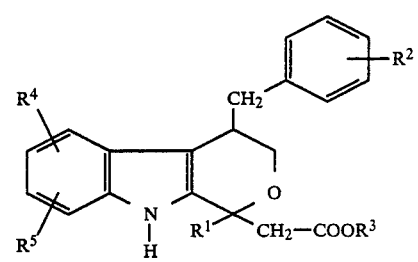
(IX)

wherein R[1], R[2], R[3], R[4] and R[5] are as defined above
(e) separating said isomer A from isomer B by crystallizing isomer A from an alcohol solvent and hydrolyzing isomer A to obtain the desired compound of formula (I).

* * * * *